United States Patent [19]

Dahlberg et al.

[11] Patent Number: 5,422,253

[45] Date of Patent: Jun. 6, 1995

[54] METHOD OF SITE SPECIFIC NUCLEIC ACID CLEAVAGE

[75] Inventors: James E. Dahlberg; Victor I. Lyamichev; Mary A. D. Brow, all of Madison, Wis.

[73] Assignee: Wisconsin Alumni Research Foundation, Madison, Wis.

[21] Appl. No.: 986,330

[22] Filed: Dec. 7, 1992

[51] Int. Cl.$^6$ .................... C12Q 1/68; C12P 19/34
[52] U.S. Cl. ..................... 435/91.53; 436/6
[58] Field of Search ................ 435/91.53, 6

[56] References Cited

U.S. PATENT DOCUMENTS 5,210,015  5/1993  Gelfand et al. ................... 435/6

FOREIGN PATENT DOCUMENTS

| 0234781 | 9/1987 | European Pat. Off. | ....... C12N 9/22 |
| 0360257 | 3/1990 | European Pat. Off. | ...... C12N 15/11 |
| 299440A5 | 4/1992 | Germany | ................ C12N 15/11 |
| 9202638 | 2/1992 | WIPO | ......................... C12Q 1/68 |
| 9206200 | 4/1992 | WIPO | ......................... C12N 15/54 |

OTHER PUBLICATIONS

Sambrook, et al. Molecular Cloning: A Laboratory Manual (1987) p. 737.

Kelly, et al., "Excision of Thymine Dimers and Other Mismatched Sequences by DNA Polymerase of *Escherichia coli*," *Nature*, 224:495–501 (Nov. 1969).

Kornberg, et al., "Enzymatic Synthesis of Deoxyribonucleic Acid, XVL Oligonucleotides as Templates and the Mechanism of Their Replication," *Biochemistry* 51:315–323 (1961).

Lundquist, et al., "Transient Generation of Displaced Single-Stranded DNA duri Nick Translation", *Cell*, 31:53–60 (1982).

Lopez, et al., "Characterization of the poIA Gene of *Streptococcus pneumoniae* and Comparison of the DNA Polymerase I It Encodes to Homologous Enzymes from *Escherichia coli* and Phage T7," *The Journal of Biological Chemistry*, 264:4255–4263 (1989).

Schachman, et al., "Enzymatic Synthesis of Deoxyribonucleic Acid," *The Journal of Biological Chemistry*, 235:3242–3249 (1960).

Setlow, et al., "Deoxyribonucleic Acid Polymerase: Two Distinct Enzymes in One Polypeptide, I. A Proteolytic Fragment Containing the Polymerase and 3'-5' Exonuclease Functions," *The Journal of Biological Chemistry*, 247: 224–231 (1972).

Setlow, et al., "Deoxyribonucleic Acid Polymerase: Two Distinct Enzymes in One Polypeptide, II. A Proteolytic Fragment Containing the 5'-3' Exonuclease Function. Restoration of Intact Enzyme Functions From the Two Proteolytic Fragments," *The Journal of Biological Chemistry*, 247:232–240 (1972).

Holland, et al., "Detection of specific polymerase chain reaction product by utilizing the 5'-3' exonuclease activity of *Thermus aquaticus* DNA polymerase," *Proc. Natl. Acad. Sci. USA*, 88:7276–7280 (1991).

Innis, et al., "DNA sequencing with *Thermus aquaticus* DNA polymerase and direct sequencing of polymerase chain reaction-amplified DNA," *Proc. Natl. Acad. Sci. USA*, 85:9436–9440 (1988).

(List continued on next page.)

Primary Examiner—Margaret Parr
Assistant Examiner—David Schreiber
Attorney, Agent, or Firm—Quarles & Brady

[57] ABSTRACT

A method of cleaving a target nucleic acid molecule is disclosed. A cleavage structure is formed that comprises the target nucleic acid and a pilot nucleic acid. A first region of the target nucleic acid is annealed to the pilot nucleic acid to form a duplex structure. A second region of the target nucleic acid contiguous to the duplex is not annealed to the pilot nucleic acid, thus forming a junction site between the duplex region and the non-annealed region. The cleavage structure is exposed to a cleavage agent capable of preferentially cleaving the cleavage structure at a target site in a manner independent of the sequence of the cleavage structure. The cleavage structure and the cleavage agent are incubated under conditions wherein cleavage can occur.

1 Claim, 7 Drawing Sheets

OTHER PUBLICATIONS

Longley, et al., "Characterization of the 5' to 3' exonuclease associated with *Thermus aquaticus* DNA polymerase", *Nucl. Acids. Res.*, 18:24:7317–7322 (1990).

Kaledin, et al., "Isolation and Properties of DNA Polymerase From the Extremely Thermophilic Bacterium," Translated from Biokhimiya, 46:1576–1584.

Li, et al., "Targeted cleavage of mRNA in vitro by RNase P from *Escherichia coli*," *Proc. Natl. Acad. Sci. USA* 89:3185–8189 (1992).

Podhajska et al., "Conversion of the FokI endonuclease to a universal restriction enzyme: cleavage of phase M13mp7 DNA at predetermined sites," *Gene*, 40:175–182 (1985).

Symons, Robert H., "Small Catalytic RNAs," *Annu. Rev. Biochem.*, 61:641–71 (1992).

Lilly and Kemper, "Cruciform-Resolvase Interactions in Supercoded DNA," *Cell* 36:413–422, 1984.

Chow, et al., "Reversal of Integration and DNA splicing mediated by integrase of human immunodeficiency virus," *Science* 255:723–726, 1992.

METHOD OF SITE SPECIFIC NUCLEIC ACID CLEAVAGE

FIELD OF THE INVENTION

The field of the present invention is molecular biological techniques for manipulating nucleic acid molecules. In particular, the field of the present invention is use of a 5' exonuclease activity of a DNA polymerase to cleave a nucleic acid molecule.

BACKGROUND

Cleavage of Nucleic Acid

Many techniques of molecular biology depend on the ability to cleave DNA or RNA molecules specifically at defined locations. Restriction enzymes cleave double-stranded DNA at specific sequences that are usually palindromic and 4-6 base pairs in length. Several hundred restriction enzymes have been discovered, most of which only cleave double-stranded DNA molecules. Several restriction enzymes have been shown to have the ability to cleave single-stranded DNA, albeit with reduced efficiency, at sites that bear the sequence that is normally recognized in double-stranded DNA. While the large number of different restriction enzymes cleave double-stranded DNA at a variety of sites, these enzymes cleave only at sites whose sequences conform to the substrate sequence specificity of the enzyme, and do not cleave at all points that might be desired by the investigator. Therefore, restriction enzymes limit a cleavage reaction to both a specific nucleotide sequence and to the use of double-stranded DNA.

Class IIs restriction enzymes, such as Fok 1, cleave DNA at a site other than their recognition sequences. Fok I can be directed to cleave single-stranded DNA at selected sites through the use of adaptor oligonucleotides that direct it to the DNA (Podhajska et al., *Gene*, 40, 175–182; 1985). The adaptor must contain two regions—one that serves as the recognition site for the enzyme and another that hybridizes to the single-stranded DNA. The specificity of the binding of the adaptor to its target may be relatively low due to the ability of the enzyme to tolerate mismatched base pairs and the need to incubate the reaction at temperatures below 40° C. Only DNA has been shown to be a substrate for cleavage in this system.

Ribozymes, RNA molecules that possess self-catalytic activity, can be targeted to cleave nucleic acid. However, the specific target cleavage sites have a sequence requirement (Symons, R. *Ann. Rev. of Biochem.*, 61:641–671, 1992).

Other methods of cleaving nucleic acids include the use of non-specific nucleases. A nuclease is an enzyme that cleaves nucleic acids. Endonucleases, such as the restriction endonucleases discussed above, cleave nucleic acids by hydrolysis of internal phosphodiester bonds. Although restriction endonucleases cleave only at specific nucleotide sequences, other endonucleases, such as Mung Bean nuclease, are not sequence-specific. In contrast, exonucleases cleave nucleic acid chains from the ends. An example of a structure-specific nuclease is snake venom phosphodiesterase I which is a nuclease that degrades single-stranded nucleic acids. Non-sequence-specific nucleases, either exonucleases or endonucleases, cannot be used directly to cleave nucleic acid molecules in a sequence specific manner.

RNA can be cleaved at specific sites through hybridization of adaptor molecules that serve as sequence-specific recognition sites for RNases such as RNaseP. (Li, et al., *Proc. Natl. Acad. Sci.*, 89:3185–3189, 1992).

There is a need in the art of molecular biology techniques for a method to cleave nucleic acids at any specific sequence that is not limited to sequences recognized by restriction endonucleases.

DNA Polymerase

DNA polymerases (DNAPs) catalyze the synthesis of a DNA chain. Additionally, many DNAPs are known to have nuclease activity.

Some DNAPs are known to remove nucleotides from the 5' and 3' ends of DNA chains (Kornberg, et al., *DNA Replication*, 2d ed., W. H. Freeman and Co., publishers, 1992). These activities are usually termed "5' exonuclease" and "3' exonuclease", respectively. For example, the 5' exonuclease activity located in the N-terminal domain of several DNAPs participates in removal of RNA primers during lagging strand synthesis during replication and the removal of damaged nucleotides during repair. Some DNAPs, such as one isolated from *E. coli* (DNAPEcl), also have a 3' exonuclease activity responsible for proof-reading during synthesis (Kornberg, supra).

A DNAP isolated from *Thermus aquaticus*, called Taq DNA polymerase (DNAPTaq), has a 5' exonuclease activity, but lacks a functional 3' exonucleolytic domain (Lawyer, et al., *J. Biol. Chem. Sci.*, 12:288, 1987). Derivatives of DNAPEcl and DNAPTaq, respectively called the Klenow (DNAPKln) and Stoffel (DNAPStf) fragments, lack 5' exonuclease domains as a result of enzymatic or genetic manipulations (Brutlag, et al., *Biochem. Biophys. Res. Commun.*, 37:982, 1969; Erlich, et al., *Science*, 252:1643, 1991; Setlow, et al., *J. Biol. Chem.*, 247:232, 1972). The 5' exonuclease activity of DNAPTaq is reported to require concurrent synthesis (D. H. Gelfand, *PCR Technology; Principles and Applications for DNA Amplification*, Henry A. Erlich, ed. Stockton Press, 17, 1989). Although mononucleotides predominate among the digestion products of the 5' exonucleases of DNAPTaq and DNAPEcl, short oligonucleotides ($\leq$12 nucleotides) can also be observed, implying that these so-called 5' exonucleases can function endonucleolytically (Setlow, supra; Holland, al. *Proc. Natl. Acad. Sci. USA.*, 88:7276, 1991). Thus, we prefer to call these activities "5' nucleases".

SUMMARY OF THE INVENTION

The present invention is a method of cleaving a single-stranded nucleic acid molecule. We refer to this single stranded nucleic acid molecule as the "target" molecule.

First, a cleavage structure is formed that comprises the target nucleic acid and a pilot nucleic acid. A first region of the target nucleic acid is annealed to the pilot nucleic acid to form a duplex structure. A second region of the target nucleic acid contiguous to the duplex is not annealed to the pilot nucleic acid, thus forming a junction site between the annealed region and the non-annealed region.

Second, this cleavage structure is exposed to a cleavage agent capable of preferentially cleaving the cleavage structure at a target site. The cleavage agent acts independently of sequence of the cleavage structure.

Third, the cleavage structure and the cleavage agent are incubated under conditions wherein cleavage can occur.

In a preferred form of the present invention, the pilot nucleic acid is covalently linked to the target molecule. In another preferred form of the present invention, the pilot nucleic acid is an oligonucleotide.

In a preferred form of the present invention the cleavage entity is an enzyme. In an especially preferred form of the present invention, the cleavage agent is a domain of a DNA polymerase. In another preferred form of the present invention, the cleavage agent is thermostable.

In another preferred form of the present invention, the third step of the method of the present invention is at a temperature between 40° C. and 85° C.

In a preferred form of the invention, the target site is within two nucleotides of the junction site.

It is an object of the present invention to cleave nucleic acid molecules, such as RNA and DNA molecules, at specific sites.

It is a feature of the present invention that a nucleic acid molecule may be cleaved at any desired location in a sequence independent manner.

It is an advantage of the present invention that the cleavage can take place at high temperatures.

It is another advantage of the present invention that cleavage sites are not restricted to specific restriction endonuclease sites.

Other objects, advantages, and features of the present invention will become apparent after examination of the specification, drawings and claims.

DESCRIPTION OF THE INVENTION

1. In General

The present invention is a method for cleaving a nucleic acid molecule. By "nucleic acid" we mean any polynucleotide. This method takes advantage of the observation that 5' nucleases of DNA polymerases (DNAPs) recognize a substrate by structure rather than sequence. This feature can be exploited to impose sequence specificity on the enzyme by annealing a targeted sequence at high temperatures to an appropriate pilot nucleic acid which directs the enzyme to cleave the substrate at the desired site. It also can be used as an indirect probe to analyze sequence or structural differences between two similar nucleic acids or complexes containing nucleic acids.

Figure 1:
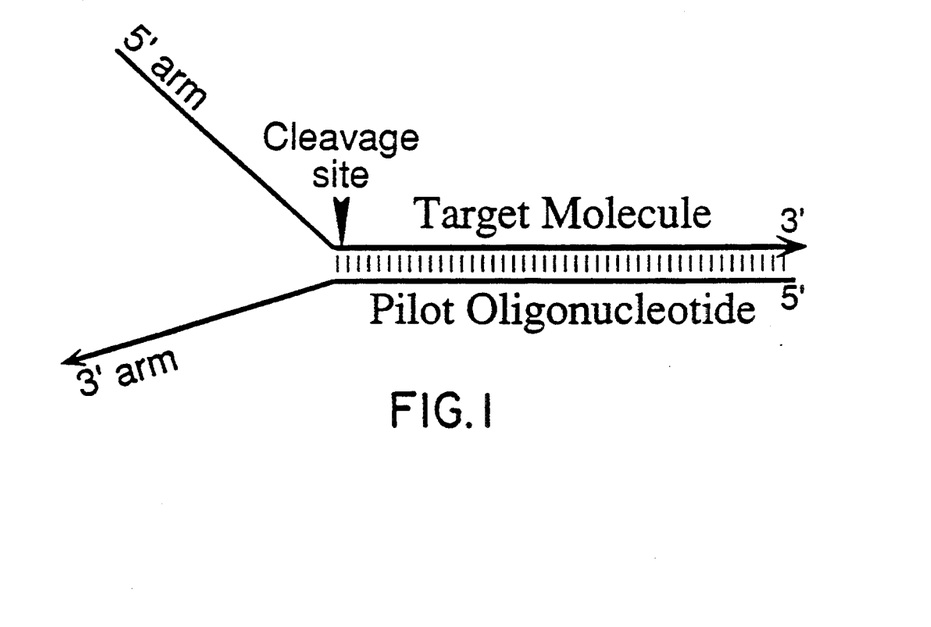
FIG. 1 is a diagram of a bifurcated duplex comprising a region of the target molecule hybridized to a complementary region of the pilot nucleic acid.

FIG. 1 is a diagram of an appropriate nucleotide substrate for the present invention. We call such appropriate substrates "cleavage structures". Referring to FIG. 1, the cleavage structure of the present invention comprises a target molecule and a pilot nucleic acid. The target nucleic acid molecule has a first region which is sufficiently complementary to anneal the pilot nucleic acid, called a pilot "oligonucleotide" in FIG. 1. After annealing, the 5' region of the target molecule of FIG. 1 is free and the 3' region of the target molecule is annealed. We call the FIG. 1 structure a "bifurcated duplex." The annealed region and the non-annealed region define a "junction site". By "junction site" we mean the site that is between the first nucleotide in duplex form and the nonannealed nucleotides.

After the annealing reaction, the annealed molecule is exposed to a cleavage agent. By "cleavage agent" we mean a molecule such as a DNAP, a domain of a DNAP, or a synthetically created protein or peptide, capable of cleaving a cleavage structure at a specific site. A preferable example of a cleavage agent is a 5' nuclease activity of DNAP, such as DNAPTaq.

After exposing the cleavage structure to a cleavage agent, the structure and agent are incubated under conditions wherein cleavage can occur. The Examples below disclose conditions suitable for the various specific cleavage agents used, such as DNAPTaq, DNAPTfl, DNAPTth and DNAPEcl. However, one skilled in the art of molecular biology would be able to determine appropriate conditions for other cleavage agents.

Figure 2:
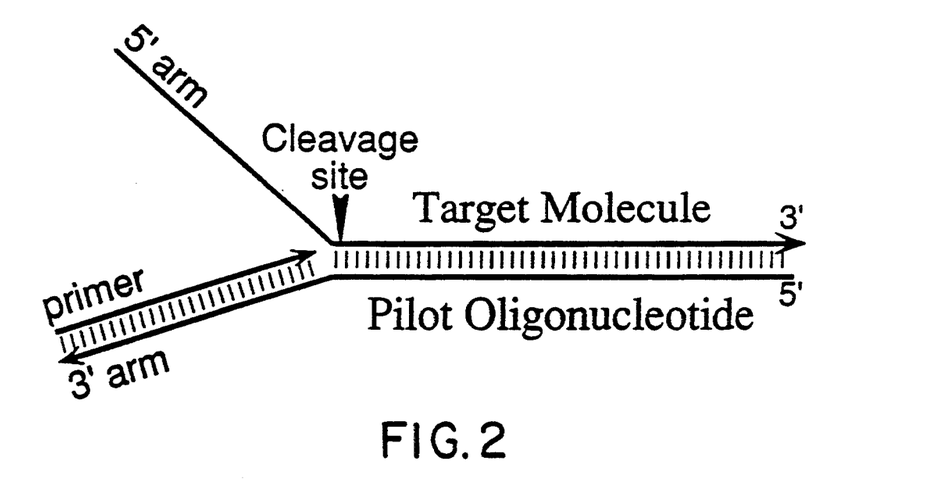
FIG. 2 is a diagram of a bifurcated duplex comprising a region of the target molecule, pilot oligonucleotide and a primer—a nucleic acid complementary to the 3' extension of the pilot nucleic acid.
Figure 3:
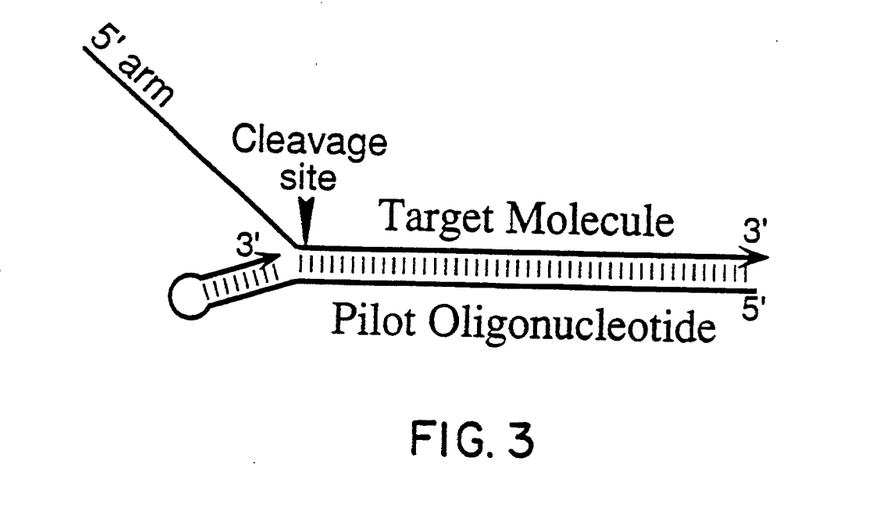
FIG. 3 is a diagram of a bifurcated duplex comprising a target molecule and pilot oligonucleotide covalently attached to a primer.
Figure 4:
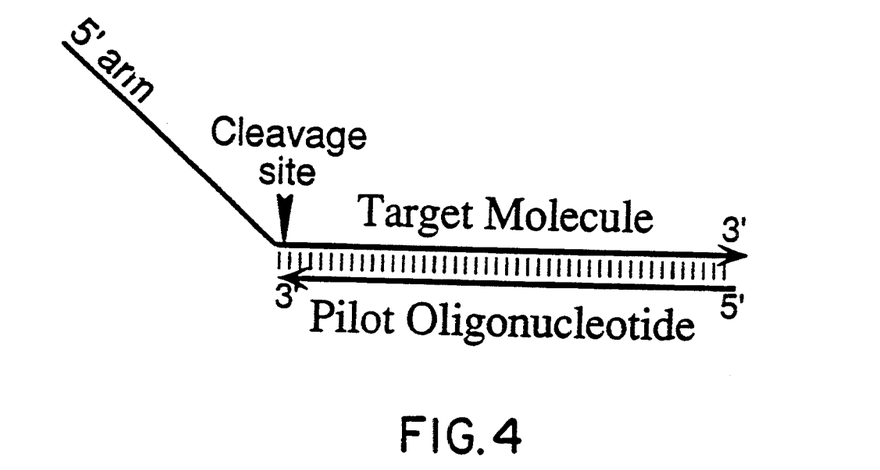
FIG. 4 is a diagram of a bifurcated duplex with no 3' extension of the pilot nucleic acid.

After the incubation, the target molecule is cleaved at the cleavage site. The exact location of the cleavage site is shown in FIGS. 1–4. When the bifurcated duplex of FIG. 1 is incubated with a cleavage agent, the cleavage site is within two nucleotides of the junction site. When a primer (described below and in FIGS. 2 and 3) is part of the cleavage structure, the cleavage site is within two nucleotides of the junction site if the primer extends to the junction site, as FIGS. 2 and 3 depict. If the primer does not extend to the junction site, the cleavage site may shift to a site within the 5' arm of the target nucleotide.

The method of the present invention requires single-stranded molecules. However, if one wishes to cleave a double-stranded molecule, one need only denature the double-stranded molecule and then make individual pilot oligonucleotides to the desired sites of cleavage in both strands.

The pilot nucleic acid may either be covalently linked to the target molecule or it may be an exogenously added nucleic acid molecule, such as an oligonucleotide. In FIG. 1, the pilot is shown as an oligonucleotide that has been added to the target molecule. However, the annealing pilot nucleic acid could be another region of the target molecule that is complementary to the first section of the target molecule.

Preferably, the cleavage agent is DNAPTaq. Our observation that the 5' nuclease of DNAPTaq is a specific endonuclease that can release long 5' extensions was unexpected since no previous studies on the 5' nuclease activities of DNAPs had reported products longer than a few nucleotides (Setlow, supra; Holland, supra). Also, the published work on the 5' nuclease of DNAPTaq indicated that this nuclease activity required concomitant synthesis (Lawyer, supra; Holland, supra). This requirement had been observed in reactions run in high concentrations of KCl, which would inhibit primer-independent cleavage, so an added primer would have to have been extended up to the cleavage site.

Preferably, the incubation step is run at a temperature between 40° C. and 85° C. and the cleavage agent is a thermostable enzyme. Because the cleavage reaction can be run at 75° C. and above when DNAPTaq or another thermostable enzyme is used, the investigator can impose a high degree of specificity on the site of cleavage by requiring that the interaction between the target and the pilot oligonucleotide be stable at high temperatures. (By "thermostable" we mean an enzyme that is stable at incubation temperatures greater than 40° C. and preferably stable at incubation temperatures greater than 70° C. for a sufficient period of time for cleavage to occur.) The high degree of sequence specificity may be useful in selection against certain templates in PCR amplification. Likewise, this specificity may find application in the production of nucleic acid fragments of an optimal size, such as those that are to be analyzed by single-strand conformation polymorphism (SSCP, Orita, et al. Genomics 5:874, 1989; K. Hayaski, *PCR Meth. and Appl.* 1:34, 1991).

Other cleavage agents that are preferable for the present invention are DNAPs from *Thermus thermophilus* and *thermus flavus*. However, the method of the present invention is also suitable for non-thermostable enzymes, such as DNAPEcl, and the incubating step may take place under temperature conditions suitable for these enzymes.

2. Cleavage of Target Nucleic Acid Molecule Using a Pilot Oligonucleotide

In a preferred embodiment of the present invention, the pilot nucleic acid component of the cleavage structure is an oligonucleotide designed to be complementary to a stretch of sequence on the 3' side of and to one nucleotide on the 5' side of the desired cleavage site. FIG. 1 describes this assembly and the specific cleavage site. If a cut in a double-stranded molecule is required, the double-stranded molecule is denatured and the procedure described below is performed on both strands, by separate pilot oligonucleotides. A preferable method of denaturing a double-stranded nucleic acid molecule is by heating the molecule to a temperature above the "melting temperature" of the molecule.

The basic procedure involves the partial annealing of a pilot oligonucleotide such that the 5' end of the pilot forms a duplex with the single-stranded target molecule, and the 3' end of the pilot is not paired to the target. This forms the bifurcated structure depicted in FIG. 1. Still referring to FIG. 1, the unpaired 5' region of the target molecule is termed the 5' arm and the unpaired 3' region of the pilot oligonucleotide is termed the 3' arm.

The complex formed is then exposed to a cleavage agent and the target molecule is cleaved in the 5' region, one nucleotide into the duplex adjacent to the 5' arm. Referring to FIG. 1, the site where the target molecule is cleaved is termed the "cleavage site."

Long 5' arms might contain structures that could inhibit cleavage. Such structures may be removed by performing the reaction at elevated temperature with a thermostable 5' nuclease.

The arrangement shown in FIG. 1 has an unpaired 3' arm. This arm may be as short as one nucleotide or it may be very long (>2500 nucleotides). Cleavage of the target molecule in this type of complex is termed "primer-independent" cleavage, reflecting the absence of a primer annealed to the 3' arm. An excess of the pilot oligonucleotide would be annealed to the target DNA, at a temperature that would preclude nonspecific binding. The reaction buffer would be chosen to maintain the appropriate pH for the enzyme, and would be low in salt. For example, if the 5' exonuclease activity of DNAPTaq is used as a cleavage agent, the buffer is adjusted to pH 8.5 (at 20° C.) and the optimal salt is around 20 mM for KCl. We have found that KCl concentrations above about 40 mM inhibit cleavage of the target molecule in the FIG. 1 structure. This salt optimum is lower than the 50 mM usually provided in forward synthesis reactions with DNAPTaq.

The annealed complex is then exposed to the cleavage agent and cleavage of the target molecule is monitored by standard methods, such as by electrophoretic mobility of substrate and products.

This mode of cleavage is also useful for detecting single- or poly-nucleotide sequence differences within the target nucleic acid. To determine if a target nucleic acid has a certain nucleotide in a specific position, within an otherwise known sequence (e.g. a specific point mutation) a pilot oligonucleotide would be designed such that it would hybridize completely to one of the sequence options, but with the other options, it would have at least one mismatched nucleotide at its extreme 3' end. Successful cleavage would indicate that the pilot is not completely complementary to the target nucleic acid.

An alternative arrangement of target nucleic acid and pilot oligonucleotide is disclosed in FIG. 2. The arrangement shown in FIG. 2 includes another oligonucleotide, which we call a "primer", annealed to the 3' arm of the pilot oligonucleotide. Preferably, the 3' end of the annealed primer is within 15 nucleotides of the junction site. More preferably, the 3' end of the primer is within 4 nucleotides of the junction site. Most preferably, the 3' end of the primer is within 1 nucleotide of the junction site.

Cleavage of this structure is termed "primer-directed" cleavage. We have experimentally determined that primer-directed cleavage occurs at a greater rate and is relatively insensitive to the salt concentration in the reaction mixture. The complex depicted in FIG. 2 has the advantage of allowing salt suppression of primer-independent cleavage (FIG. 1). Therefore, cleavage at fortuitous secondary structures can be suppressed by inclusion of KCl at concentration equal to or greater than 50 mM.

The primer can be of any convenient sequence, provided that the primer/pilot duplex is long enough to be stable at the temperature chosen for the pilot/target annealing and is preferably at high enough concentration to saturate all of the pilot oligonucleotide 3' arms. To cleave a target molecule at a specific site, a reaction would be assembled as described for primer-independent cleavage, above. In a preferred form of the present invention, the concentration of KCl can be increased to 50 mM, or higher, to suppress cleavage at any structures lacking primers. After exposure to an enzyme with 5' nuclease activity, cleavage can be monitored as described above.

Another option for primer directed cleavage is depicted in FIG. 3. In this case, the pilot oligonucleotide has a 3' terminal hairpin that acts as an integral primer. The looped end of the hairpin may be of a specific sequence called a tetra-loop, which confers extraordinary thermostability on the stem-loop structure (Antao et al., *Nucl. Acids Res.*, 19:5901, 1991). When the primer is covalently linked to the pilot nucleic acid the presence of a primer annealed to the 3' arm is not a function of the primer concentration. Cleavage of a target molecule in the presence of such a pilot has all of the advantages of a primer directed cleavage, such as salt suppression of random cleavage, and requires the addition of only one oligonucleotide.

Cleavage of an RNA target molecule can be achieved by formation of all of the complexes described above and, additionally, the one depicted in FIG. 4, in which the pilot oligonucleotide does not have a free 3' arm. This arrangement has the advantage that oligonucleotides designed for hybridization and/or reverse transcription may also be used as pilot oligonucleotides, and vice versa, if appropriate to the experiment.

Uses for RNA cleavage include creation of fragments of RNA for structural studies or for subsequent translation in the study of truncated proteins. In the method of the present invention, the 5' nuclease cleaves the RNA at a single, predictable site, in contrast to previously described RNAse H, which cleaves the RNA at several sites along an RNA/DNA heteroduplex. The reaction is assembled as described above for the DNA cleavages, and is performed under the higher salt conditions usually used for the primer-directed cleavage.

3. Cleavage of a Target Nucleic Acid with Internal Annealing

The cleavage method of the present invention can be used to cleave a molecule in which there is some internal homology so that a part of the molecule will anneal with another part of the molecule. This situation is useful to detect internal sequence differences in DNA fragments without prior knowledge of the specific sequences of the variants. The bifurcated duplex structure which identifies a nucleic acid as a substrate for the 5' nuclease can be created by allowing a single stranded molecule to fold upon itself. Such a folded structure could resemble those shown in FIGS. 1-3, except that the 3'-end of the target molecule and the 5'-end of the pilot nucleic acid would be covalently linked. The conformation assumed by a single strand when it folds on itself depends upon the length, the specific sequence, the temperature of the reaction, and the presence of salts and other solutes that either stabilize or disrupt the base-pairing.

Changes as small as a single nucleotide within a strand of nucleic acid up to about 300 nucleotides long can alter the folding structure of that molecule sufficiently to be detected by an altered mobility during non-denaturing gel electrophoresis (Single Strand Conformation Polymorphism, SSCP), and the changes are of individual enough character to allow discrimination among many closely related molecules. This same alteration of structure can be assessed by altered patterns of cleavage using this method. One might use this type of analysis to examine human genetic variation, such as allelic differences, or to analyze simpler organisms, such as in the characterization of different isolates of a highly varied or a rapidly mutating virus.

A specific fragment of RNA or DNA would be isolated from the organism by directed 5' nuclease cleavage, by restriction digestion or by in vitro amplification (such as in vitro transcription for RNA, or PCR for DNA). The material would be denatured by heating, if double-stranded, and the reaction would be dilute enough to minimize immediate re-annealing of complementary strands and to favor intramolecular interactions. The reactions would be performed in a buffered solution, of pH appropriate to the enzyme used, and would be low in salt, to permit cleavage of substrate structures that might adventitiously form along the DNA strand. This material would be exposed to a cleavage agent, with the temperature and duration of the reaction determined empirically to give a desirable number of cleavage products. Reactions performed at lower temperatures may require longer incubations to compensate for reduced rates of cleavage. The products of the reaction would then be analyzed and compared to relevant standards and controls. The assay could be electrophoretic separation, with visualization by autoradiography, or by transfer to a hybridization membrane with subsequent probing.

When a characteristic cleavage pattern that reflects the structure of the molecule of interest has been established for a given fragment of nucleic acid, the cleavage reaction of the present invention can be used as an assay for changes in that structure. One kind of change, mentioned above, comes from altering some portion of the sequence of the nucleic acid itself, as would be observed in analysis of a mutation, or of an allelic variation. Another kind of change could be induced by the binding of a foreign entity to the nucleic acid before the cleavage analysis. Examples of foreign entities include pieces of complementary nucleic acids (i.e. RNA or DNA probes), proteins (e.g. nucleic acid binding proteins), or anything else that might be expected to interact with a nucleic acid molecule of interest.

For example, to observe the effect of an oligonucleotide on the structure of nucleic acid, the target molecule would be heat-denatured, as above, and cooled down to the reaction temperature in the presence of an excess of a complementary oligonucleotide, all in the appropriate salts and buffers. At reaction temperature, the cleavage agent would be added, and allowed to interact with the nucleic acid for the length of time predetermined on free nucleic acid. Control reactions missing the oligonucleotide or the nuclease would be performed in parallel. At the end of the incubation period, the reactions would be stopped, such as by the addition of enough EDTA to inactivate the enzyme, and would be assayed, as above, for the cleavage patterns.

We note that the added foreign entity need not interact with the cleavage site directly. It need only interact with the target fragment in such a way as to alter the structure or the accessibility of potential cleavage sites. For example, an added oligonucleotide might sequester a region of the fragment that would otherwise contribute to or inhibit the formation of a cleavable structure. Also, such an oligonucleotide might participate in the cleavage as a pilot or primer oligonucleotide at sites within the target molecule. The only requirement for a foreign entity in these types of experiments is that it behaves in a consistent and repeatable way on a given fragment of nucleic acid, under given reaction conditions.

4. Suitable Cleavage Agents

The present invention requires a cleavage agent that is able to cleave a bifurcated duplex at the desired cleavage site. A suitable cleavage agent will be able to cleave a bifurcated duplex in a sequence-independent manner. Restriction endonucleases that are only able to cleave at a specific sequence are not suitable cleavage agents. Particularly suitable nucleases are contained in thermostable enzymes such as DNAPTaq, DNAPTfl and DNAPTth. Non-thermostable enzymes, such as DNAPEcl, are also suitable for the present invention. We envision that the gene 6 protein from bacteriophage T7 is also a suitable cleavage agent.

Figure 5:
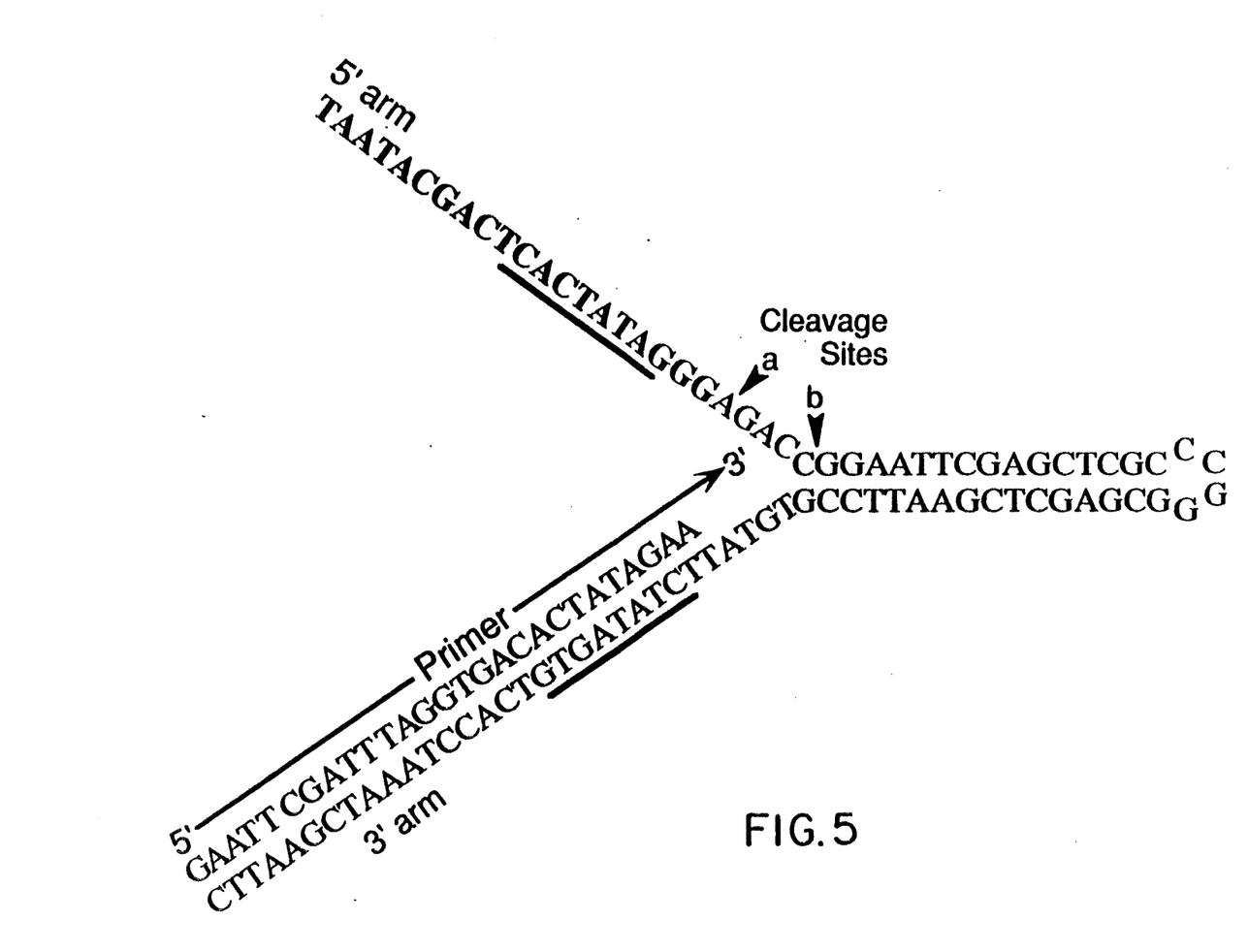
FIG. 5 is the nucleotide sequence of an exemplary bifurcated duplex and primer.

If one wishes to determine whether or not a particular agent is suitable for the present invention, one can test whether the agent has the ability to recognize and cleave bifurcated duplex substrates. A candidate enzyme can be tested for structure-specific cleavage activity by exposing it to test complexes that have the structures shown in FIGS. 1-4. An example of an appropriate nucleotide sequence is presented at SEQ ID NO: 1 and in FIG. 5. A primer oligonucleotide, illustrated in FIG. 5, complementary to the 3' arm is preferred for these tests. The sequence of the FIG. 5 primer oligonucleotide is presented in SEQ ID NO: 2. Referring to FIG. 5, cleavage at site "a" will be obtained when the primer is not extended to the junction site. Cleavage at site "b" will be obtained when the primer is extended to the junction site.

The complete test involves three test reactions: 1) a primer-directed cleavage (FIG. 2 and FIG. 5) is tested because it is relatively insensitive to variations in the salt concentration of the reaction and can, therefore, be performed in whatever solute conditions the candidate enzyme normally requires for activity; 2) a similar primer-directed cleavage is performed in a buffer that would permit primer-independent cleavage, i.e. a low salt buffer, to demonstrate that the enzyme is viable under these conditions, and 3) a primer-independent cleavage (FIG. 1 and FIG. 5 without the addition of the primer) is performed in the same low salt buffer.

Suitable DNA substrates can be chemically synthesized or can be generated by standard recombinant DNA techniques. By the latter method, the hairpin portion of the molecule can be created by inserting into a cloning vector duplicate copies of a short DNA segment, adjacent to each other but in opposing orientation. The double-stranded fragment encompassing this inverted repeat, and including enough flanking sequence to give short (about 20 nucleotides) unpaired 5' and 3' arms, can then be released from the vector by restriction enzyme digestion, or by PCR performed with an enzyme lacking a 5' exonuclease (e.g. the Stoffel fragment of Amplitaq TM DNA polymerase, Vent TM DNA polymerase).

The test DNA can be labeled on either end, or internally, with either a radioisotope or with a non-isotopic tag. Whether the hairpin DNA is a synthetic single strand, or a cloned double strand, the DNA is heated prior to use to melt all duplexes. When cooled on ice, the structure depicted in FIG. 5 is formed. This structure is stable for sufficient time to perform these assays.

For Test 1, described above, a detectable quantity of the test molecule and preferably a 10 to 100-fold molar excess of primer are placed in a buffer known to be compatible with the test enzyme. For Test 2, the same quantities of molecules are placed in a solution that is the same as the buffer above regarding pH, enzyme stabilizers (e.g. bovine serum albumin, nonionic detergents, gelatin) and reducing agents (e.g. dithiothreitol, 2-mercaptoethanol) but that replaces any salt with 20 mM KCl. Buffers for enzymes that usually operate in the absence of salt are not supplemented to achieve this concentration. For Test 3, the same quantity of the test molecule, but no primer, are combined under the same buffer conditions used for Test 2.

All three test reactions are then exposed to enough of the enzyme that the molar ratio of enzyme to test complex is approximately 1:1. The amount of enzyme needed can be calculated from the specific activity (units/mg) given by the manufacturer and the molecular weight. In our hands, 0.5 units per 0.01 pmoles of target has always worked, regardless of what the molar ratios were. The reactions are incubated at a range of temperatures up to, but not exceeding, the temperature allowed by either the enzyme stability or the complex stability, whichever is lower, probably up to 72° C. for enzymes from thermophiles, for a time sufficient to allow cleavage (10 to 60 minutes). The products of Tests 1, 2 and 3 are typically resolved by denaturing polyacrylamide gel electrophoresis, and visualized by autoradiography or by a comparable method appropriate to the labeling system used.

Release of the 5' arm as a discreet oligonucleotide or group of oligonucleotides indicates successful internal cleavage.

With the DNAPTaq, Test 1 is performed in a buffer of 10 mM Tris-Cl, pH 8.5 at 20° C., 1.5 mM $MgCl_2$ and 50 mM KCl, while in Tests 2 and 3 the KCl concentration is reduced to 20 mM. In tests 1 and 2, when 10 fmoles of the test molecule of FIG. 5 is combined with 1 pmole of the indicated primer, incubation for 10 minutes at 55° C. is sufficient for 0.1 units of the enzyme to cleave completely. In Test 3, incubation for 10 minutes at 72° C. gives complete cleavage of the same amount of this molecule, in the absence of primer. In both cases, the products of the reaction are stable during extended incubations (>60 minutes), provided that no contaminating nucleases are present, so overdigestion is unlikely. When the molecule shown in FIG. 5 is labeled at the 5' end, the released 5' fragment, 21 or 25 nucleotides long, is conveniently resolved on a 20% polyacrylamide gel (19:1 crosslinked) with 7M urea, in a buffer of 45 mM Trisborate pH 8.3, 1.4 mM EDTA.

Some enzymes or enzyme preparations may have associated or contaminating activities that may be functional under the cleavage conditions described above, and may interfere with 5' nuclease detection. Reaction conditions may need to be modified in consideration of these other activities, to avoid destruction of the substrate or other masking of the 5' nuclease cleavage and its products. For example, the DNA polymerase I of *E. coli* (DNAPEcl), in addition to its 5' nuclease and polymerase activities, has a 3' exonuclease that can degrade DNA in a 3' to 5' direction. Consequently, when the molecule in FIG. 5 is exposed to this polymerase under the conditions described above, the 3' exonuclease quickly removes the 3' arm, destroying the bifurcated structure required of a substrate for the 5' nuclease cleavage, and no cleavage is detected. The true ability of DNAPEcl to cleave the structure can be revealed if the 3' exonuclease is inhibited by a change of conditions (e.g., change in reaction pH), mutation, or by addition of a competitor for the activity. Addition of 100 pmoles of a single-stranded competitor oligonucleotide unrelated to the target molecule, to the cleavage reaction with DNAPEcl effectively inhibits the digestion of the 3' arm of the molecule of FIG. 5, without interfering with the 5' nuclease release of the 5' arm. The concentration of the competitor is not critical, but should be high enough to occupy the 3' exonuclease for the duration of the reaction.

Similar destruction of the test molecule may be caused by contaminants in the candidate nuclease preparation. Several sets of these tests may be necessary to determine the purity of the candidate nuclease, and to find the window between under and over exposure of the test molecule to the preparation being investigated.

EXAMPLES

A. 5' Nuclease of DNAPTaq

During the polymerase chain reaction (PCR) (Saiki, et al., Science 239:487, 1988; Mullis et al., Methods Enzymol. 155:335, 1987) DNAPTaq is able to amplify many, but not all, DNA sequences. One sequence that we were unable to amplify using DNAPTaq is the longer sequence shown in FIG. 5. This DNA sequence has the distinguishing character of being able to fold on itself to form a hair-pin with two single-stranded arms, which correspond to the primers used in PCR.

To test whether this failure to amplify is due to the 5' nuclease activity of the enzyme, we compared the abilities of DNAPTaq and DNAPStf to amplify this DNA sequence during 30 cycles of PCR. Synthetic oligonucleotides were obtained from The Biotechnology Center at the University of Wisconsin-Madison. The DNAPTaq and DNAPStf were from Perkin Elmer-Cetus. Polymerase chain reactions comprised 1 ng of plasmid target DNA, 5 pmoles of each primer, 40 $\mu$M each dNTP, and 2.5 units of DNAPTaq or DNAPStf, in a 50 $\mu$l solution of 10 mM Tris·Cl pH 8.3. The DNAPTaq reactions included 50 mM KCl and 1.5 mM MgCl$_2$ while the DNAPStf reactions included 10 mM KCl and 4 mM MgCl$_2$. The temperature profile was 95° C. for 30 sec., 55° C. for 1 min. and 72° C. for 1 min., through 30 cycles. Ten percent of each reaction was analyzed by gel electrophoresis through 6% polyacrylamide (cross-linked 29:1) in a buffer of 45 mM Tris-Borate, pH 8.3, 1.4 mM EDTA.

Figure 6:
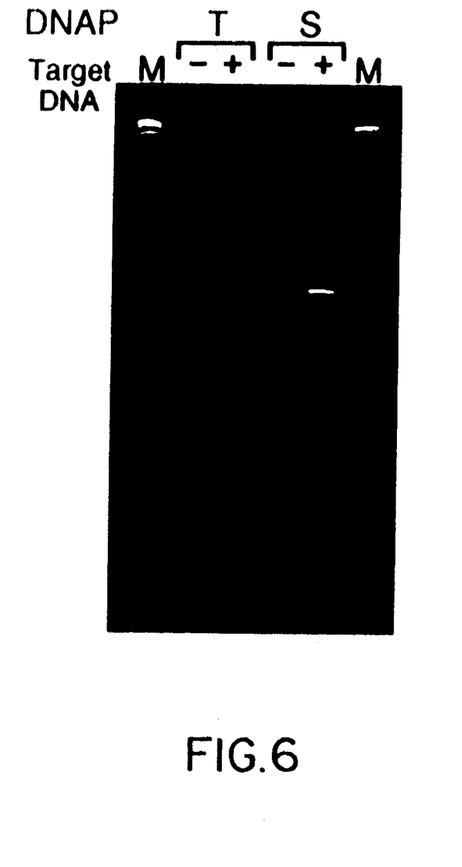
FIG. 6 is a stained gel demonstrating attempts to amplify a bifurcated duplex with DNAPTaq or DNAPStf.

Our results are shown in FIG. 6. The expected product was made by DNAPStf but not by DNAPTaq. We conclude that the 5' nuclease activity of DNAPTaq is responsible for the lack of amplification of this DNA sequence.

Figure 7:
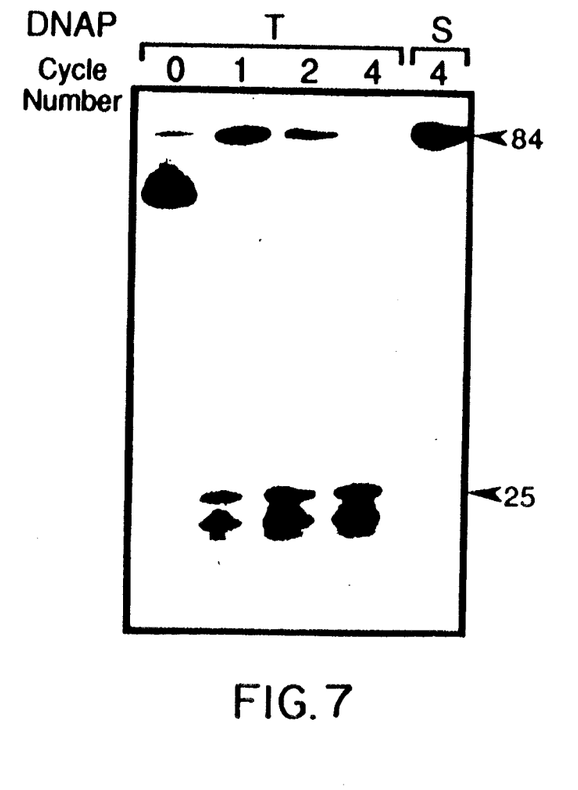
FIG. 7 is an autoradiogram of a gel analyzing the cleavage of a bifurcated duplex by DNAPTaq and lack of cleavage by DNAPStf.

To test whether the 5' unpaired nucleotides in the substrate region of this structured DNA are removed by DNAPTaq, we compared the fate of the end-labeled 5' arm during four cycles of PCR using the same two polymerases (FIG. 7). The hairpin template described in FIG. 5 was made using DNAPStf and a $^{32}$P-5'-end-labeled primer. The 5'-end of the DNA was released as a few large fragments by DNAPTaq but not by DNAPStf. The sizes of these fragments (based on their mobilities) show that they contain most or all of the unpaired 5' arm of the DNA. Thus, we learned that cleavage occurs at or near the base of the bifurcated duplex. These released fragments terminate with 3' OH groups, as evidenced by direct sequence analysis, and the ability of the fragments to be extended by terminal deoxynucleotidyl transferase.

FIGS. 8–10 are different combinations of reaction components and demonstrate our characterization of the present invention. Unless otherwise specified, the cleavage reactions comprised 0.01 pmoles of heat-denatured, end-labeled hairpin DNA (with the unlabeled complementary strand also present), 1 pmole primer (complementary to the 3' arm) and 0.5 units of DNAPTaq (estimated 0.026 pmoles) in a total volume of 10 $\mu$l of 10 mM Tris·Cl, pH 8.5, 50 mM KCl, 1.5 mM MgCl$_2$. As indicated, some reactions had different concentrations of KCl, and the precise times and temperatures used in each experiment are indicated in the individual FIGURES and legends. The reactions that included a primer used the one shown in FIG. 5. In some instances, the primer was extended to the junction site through the use of polymerase and appropriate dNTPs.

Reactions were initiated at the final reaction temperature by the addition of either the MgCl$_2$ or enzyme. Reactions were stopped at their incubation temperatures by the addition of 8 $\mu$l of 95% formamide with 20 mM EDTA and 0.05% marker dyes. Tm calculations listed were made using the Oligo ™ primer analysis software from National Biosciences, Inc., Plymouth, Minn. These were determined using 0.25 $\mu$M as the DNA concentration, at either 15 or 65 mM total salt (the 1.5 mM MgCl$_2$ in all reactions was given the value of 15 mM salt for these calculations).

Figure 8A:
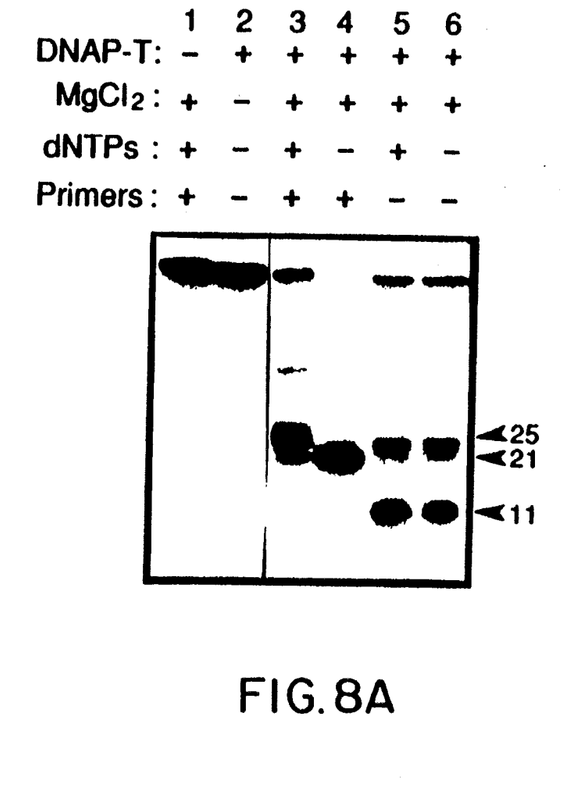
FIG. 8 is a set of autoradiograms of gels analyzing cleavage or lack of cleavage upon addition of different reaction components and change of incubation temperature during attempts to cleave a bifurcated duplex with DNAPTaq. Panel A depicts the results of cleavage assays run in the presence or absence of DNAP Taq, MgCl$_2$, dNTPs or primers. Panel B depicts the results of cleavage assays at different temperatures.
Figure 8B:
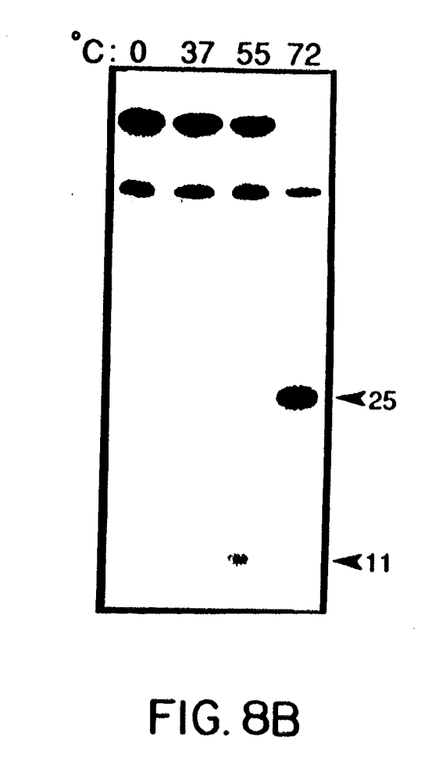

FIG. 8 is an autoradiogram containing the results of a set of experiments designed to determine the effects of reaction components and conditions on the cleavage site. FIG. 8A is a determination of reaction components required for cleavage. Incubation of 5'-end-labeled hairpin DNA was for 30 minutes at 55° C., with the indicated components. The products were resolved by denaturing polyacrylamide gel electrophoresis and the lengths of the products, in nucleotides, are indicated. FIG. 8B describes the effect of temperature on the site of cleavage in the absence of added primer. Reactions were incubated in the absence of KCl for 10 minutes at the indicated temperatures. The lengths of the products, in nucleotides, are indicated.

Surprisingly, we learned that cleavage by DNAPTaq requires neither a primer nor dNTPs (see FIG. 8A). Thus, the 5' nuclease activity can be uncoupled from polymerization. Nuclease activity requires magnesium ions, though manganese ions can be substituted without loss of activity. Neither zinc nor calcium ions support the cleavage reaction. The reaction occurs over a broad temperature range, from 25° C. to 85° C., with the rate of cleavage increasing at higher temperatures.

Still referring to FIG. 8, in the absence of added dNTPs the primer influences both the site and the rate of cleavage of the hairpin, although the primer is not elongated under these conditions. The change in the site of cleavage (FIG. 8A) apparently results from disruption of a short duplex formed between the arms of the DNA substrate. In the absence of primer, the sequences indicated by underlining in FIG. 5 could pair, forming an extended duplex. Cleavage at the end of the extended duplex would release the 11 nucleotide fragment seen on the FIG. 8A lanes with no added primer. Addition of excess primer (FIG. 8A, lanes 3 and 4) or incubation at an elevated temperature (FIG. 8B) disrupts the short extension of the duplex and results in a longer 5' arm and, hence, longer cleavage products.

The location of the 3' end of the primer can influence the precise site of cleavage. We learned by electrophoretic analysis that in the absence of primer (FIG. 8B), cleavage occurs at the end of the substrate duplex (either the extended or shortened form, depending on the temperature) between the first and second base pairs. When the primer extends up to the base of the duplex, cleavage also occurs one nucleotide into the duplex. However, when a gap of four or six nucleotides exists between the 3' end of the primer and the substrate duplex, the cleavage site is shifted four to six nucleotides in the 5' direction. This shifting of the cleavage site in concert with the location of the 3' end of the primer may result from extension of the substrate duplex through formation of short, imperfect duplexes between the 5' arm and the single-stranded gap downstream of the primer. This explanation is consistent with our observation that substrates with different sequences in this region behave in nonidentical but similar fashions.

Figure 9A:
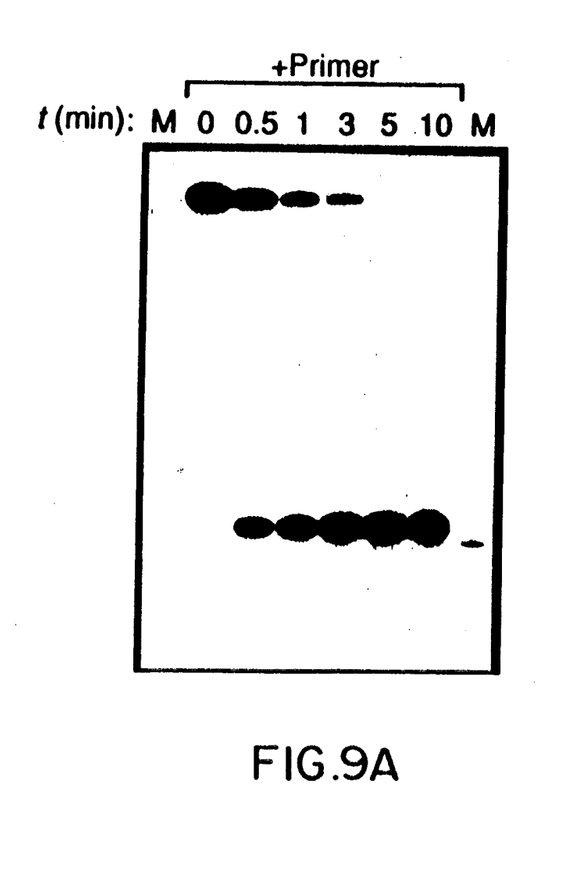
FIG. 9 is an autoradiogram displaying timed cleavage reactions, with and without primer. Panel A depicts reactions with or without added primer, as indicated. Panel B depicts reactions without added primer.
Figure 9B:
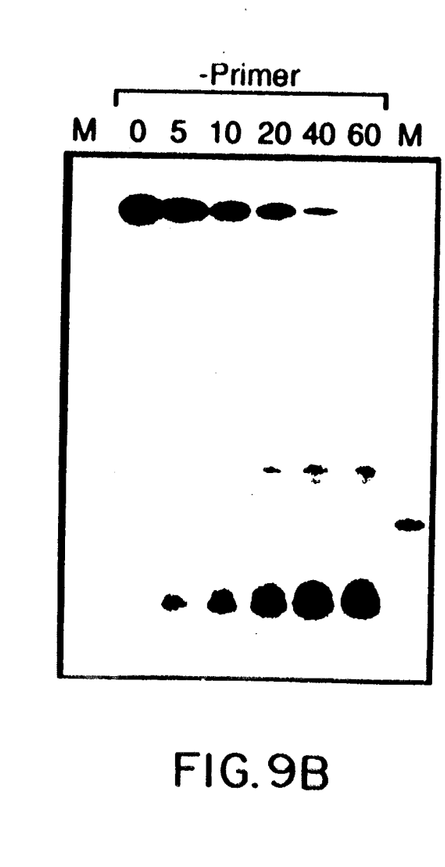

FIG. 9 describes the kinetics of cleavage in the presence (FIG. 9A) or absence (FIG. 9B) of a primer oligonucleotide. The reactions were run at 55° C. with either 50 mM KCl (FIG. 9A) or 20 mM KCl (FIG. 9B). The reaction products were resolved by denaturing polyacrylamide gel electrophoresis and the lengths of the products, in nucleotides, are indicated. "M", indicating a marker, is a 5' end-labeled 19-nt oligonucleotide. Under these salt conditions FIGS. 9A and B indicate that the reaction appears to be about twenty times faster in the presence of primer than in the absence of primer. This effect on the efficiency may be attributable to proper alignment and stabilization of the enzyme on the substrate.

The relative influence of primer on cleavage rates becomes much greater when both reactions are run in 50 mM KCl. We have determined that in the presence of primer, the rate of cleavage increases with KCl concentration, up to about 50 mM. However, inhibition of this reaction in the presence of primer is apparent at 100 mM and is essentially complete at 150 mM KCl. In contrast, in the absence of primer the rate is enhanced by concentrations of KCl up to 20 mM, but it is reduced at concentrations above 30 mM. At 50 mM KCl, the reaction is almost completely inhibited. The inhibition of cleavage by KCl in the absence of primer is affected by temperature, being more pronounced at lower temperatures.

Recognition of the 5' end of the arm to be cut appears to be an important feature of substrate recognition. We have been unable to cleave substrates that lack a free 5' end, such as circular M13 DNA. Even with substrates with defined 5' arms, the rate of cleavage by DNAPTaq is influenced by the length of the arm. In the presence of primer and 50 mM KCl, cleavage of a 5' extension that is 28 nucleotides long is essentially complete within 2 minutes at 55° C. In contrast, cleavages of molecules with 5' arms of 80 and 191 nucleotides are only about 90% and 40% complete after 20 minutes. Incubation at higher temperatures reduces the inhibitory effects of long extensions indicating that secondary structure in the 5' arm or a heat-labile structure in the enzyme may inhibit the reaction. A mixing experiment, run under conditions of substrate excess, shows that the molecules with long arms do not preferentially tie up the available enzyme in non-productive complexes. These results may indicate that the 5' nuclease domain gains access to the cleavage site at the end of the bifurcated diplex by moving down the 5' arm from one end to the other. Longer 5' arms would be expected to have more adventitious secondary structures (particularly when KCl concentrations are high), which would be likely to impede this movement.

Cleavage does not appear to be inhibited by long 3' arms of either target molecule or pilot nucleic acid, at least up to 2 kilobases. At the other extreme, we have found that 3' arms of the pilot nucleic acid as short as one nucleotide can support cleavage in a primer-independent reaction, albeit rather inefficiently. Fully paired oligonucleotides do not elicit cleavage of DNA templates during primer extension.

The ability of DNAPTaq to cleave molecules even when the complementary strand contains only one unpaired 3' nucleotide may be useful in optimizing allele-specific PCR. PCR primers that have unpaired 3' ends could act as pilot oligonucleotides to direct selective cleavage of unwanted templates during preincubation of potential template-primer complexes with DNAPTaq in the absence of nucleoside triphosphates.

B. 5' Nuclease Activities of Other DNAPS

To determine whether other 5' nucleases in other DNAPs would be suitable for the present invention, we tested an array of enzymes, several of which were reported in the literature to be free of apparent 5' nuclease activity. These were tested on the hairpin substrate shown in FIG. 5 under conditions reported to be optimal for synthesis by each enzyme.

DNAPEcl and DNAPKln were obtained from Promega Corporation; the DNAP of *Pyrococcus furious* (DNAPPfu, Bargseid, et al., *Strategies* (Stratagene, La Jolla, Calif.,) 4:34,1991) was from Stratagene, the DNAP of *Thermococcus litoralis* (DNAPTli, Vent TM (exo-), Perler, et al., *Proc. Natl. Acad. Sci. USA* 89:5577, 1992) was from New England Biolabs, the DNAP of *Thermus flavus* (DNAPTfl, Kaledin, et al., *Biokhimiya* 46:1576, 1981) was from Epicentre Technologies, and the DNAP of *Thermus thermophilus* (DNAPTth, Carballeira, et al., *Biotechniques* 9:276, 1990; Myers et. al., *Biochemistry* 30, 7661, 1991) was from U.S. Biochemicals.

0.5 units of each DNA polymerase was assayed in a 20 $\mu$l reaction, using either the buffers supplied by the manufacturers for the primer-dependent reactions, or 10 mM Tris·Cl, pH 8.5, 1.5 mM $MgCl_2$, and 20 mM KCl for primer-independent reactions. Reactions using DNAPEcl and DNAPKln were done in 5 mM Tris·Cl, pH 7.5, 5 mM $MgCl_2$, 0.1 mM DTT, with 100 pmole of 20 mer oligonucleotide and reaction mixtures were at 37° C. before the addition of enzyme.

Figure 10A:
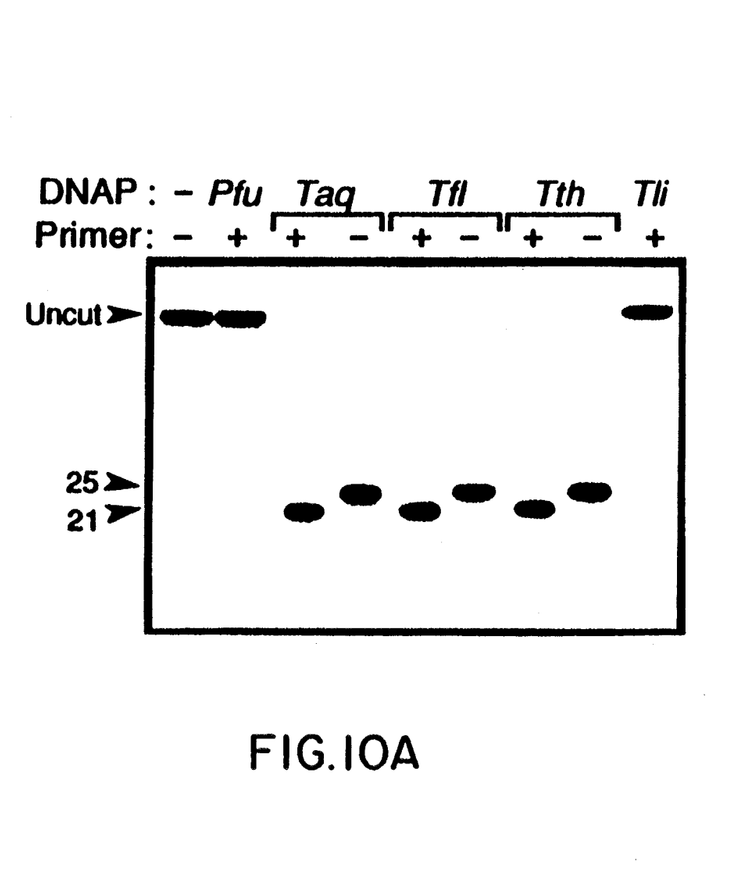
FIG. 10 is an autoradiogram of a gel demonstrating attempts to cleave a bifurcated duplex (with and without primer) with various DNAPs. Panel A depicts assays with Pfu, Taq, Tfl, Tth, and Tli polymerases. Panel B depicts assays with Taq, Ecl, and Kln polymerases.
Figure 10B:
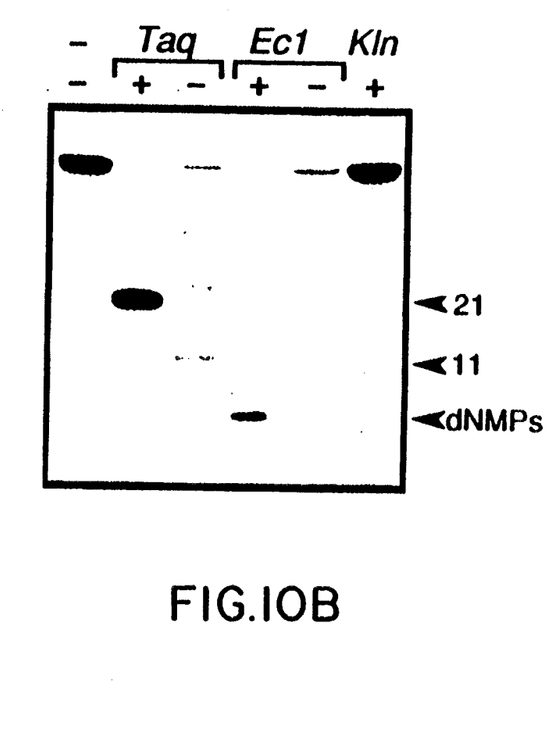

FIG. 10 is an autoradiogram recording the results of these tests. FIG. 10 A demonstrates reactions of endonucleases of DNAPs of several thermophilic bacteria. The reactions were incubated at 55° C. for 10 minutes in the presence of primer or at 72° C. for 30 minutes in the absence of primer, and the products were resolved by denaturing polyacrylamide gel electrophoresis. The lengths of the products, in nucleotides, are indicated. FIG. 10B demonstrates endonucleolytic cleavage by the 5' nuclease of DNAPEcl. The DNAPEcl and DNAPKln reactions were incubated for 5 minutes at 37° C. Note the light band of cleavage products of 25 and 11 nucleotides in the DNAPEcl lanes (made in the presence and absence of primer, respectively). FIG. 6B also demonstrates DNAPTaq reactions in the presence (+) or absence (−) of primer. These reactions were run in 50 mM and 20 mM KCl, respectively, and were incubated at 55° C. for 10 minutes.

Referring to FIG. 10A, DNAPs from the eubacteria *Thermus thermophilus* and *Thermus flavus* cleave the substrate at the same place as DNAPTaq, both in the presence and absence of primer. In contrast, DNAPs from the archaebacteria *Pyrococcus furiosus* and *Thermococcus litoralis* are unable to cleave the substrates endonucleolytically. The DNAPs from *Pyrococcus furious* and *Thermococcus litoralis* share little sequence homology with eubacterial enzymes (Ito, et al., *Nucl. Acids. Res.* 19:4045, 1991; Mathur, et al., *Nucl. Acids. Res.* 19:6952, 1991; see also Perler, et. al. Referring to FIG. 10B, DNAPEcl also cleaves the substrate, but the resulting cleavage products are difficult to detect unless the 3' exonuclease is inhibited. The amino acid sequences of the 5' nuclease domains of DNAPEcl and DNAPTaq are about 38% homologous (Gelfand, supra).

The 5' nuclease domain of DNAPTaq also shares about 19% homology with the 5' exonuclease encoded by gene 6 of bacteriophage T7 (J. J. Dunn et al. *J. Mol. Biol.*, 166:477, 1983). We have found that this nuclease, which is not covalently attached to a DNAP polymerization domain, is also able to cleave DNA endonucleolytically, at a site similar or identical to the site that is cut by the 5' nucleases described above, in the absence of added primers. The nature of this 5' exonuclease precludes testing in the presence of a primer; a primer duplexed to the 3' arm would be a substrate for this activity.

C. Transcleavage

A cleavage substrate may also be made from separate polynucleotides, comprising a targeted nucleic acid and a pilot oligonucleotide designed to direct the nuclease to the target through formation of a substrate structure at the desired point of cleavage. The resulting substrate complex would contain a duplex with a 3' extension opposite the desired site of cleavage.

To demonstrate that cleavage could be directed by a pilot oligonucleotide, we incubated a single-stranded target DNA with DNAPTaq in the presence of two potential pilot oligonucleotides. The trans-cleavage reactions, where the target and pilot nucleic acids are not covalently linked, includes 0.01 pmoles of single end-labeled substrate DNA, 1 unit of DNAPTaq and 5 pmoles of pilot oligonucleotide in a volume of 20 μl of the same buffers. These components were combined during a one minute incubation at 95° C., to denature the PCR-generated double-stranded substrate DNA, and the temperatures of the reactions were then reduced to their final incubation temperatures. These two oligonucleotides, called 30-12 and 19-12, have 30 or 19 nucleotides complementary to the DNA, respectively, plus 12 nucleotide extensions at their 3' ends that could form short hair-pins. Oligonucleotides 30-12 and 19-12 can hybridize to regions of the DNA that are 85 and 27 nucleotides from the 5' end of the targeted strand.

As predicted, incubation of 30-12 with a mixture of 5'-labeled target DNA and DNAPTaq results in the production of a fragment of the DNA 85 nucleotides long. Cleavage does not occur at 80° C., which is above the calculated melting temperature of the duplex, although the cleavage activity is still active at that temperature (as assayed using a more stable, long, self-complementary hairpin). At 55° C., several new cleavage products accumulate in the absence of added pilot oligonucleotide. We attribute this accumulation to adventitious formation of duplexes between complementary sequences within the DNA target which could serve as substrates for cleavage. These products are not observed when the reaction is run in the presence of 50 mM KCl, which suppresses cleavage in the absence of appropriate primers or when either of the pilot oligonucleotides is present.

The specificity of targeted cleavage was tested by analysis of the products made in response to incubation with 19-12 and 30-12 at different temperatures. The calculated Tm for a duplex between 19-12 and its complement is just under 50° C. in the absence of KCl. As expected, incubation of the DNA with DNAPTaq and 19-12 results in formation of a 27 nucleotide-long cleavage product at 50° C., but not at 75° C. The yield of this product increases upon the addition of KCl, which raises the Tm well above 50° C., and, thus, increases the concentration of substrate complexes at that temperature. Substitution of 30-12 for 19-12 results in release of the 85 nucleotide product in all cases. A nonspecific oligonucleotide with no complementarity to the DNA target (but with the potential to form a hairpin with a tetra-loop at its 3' end), called 0-20, has no effect on cleavage at 50° C., either in the absence or presence of 50 mM KCl. Thus, the specificity of cleavage reactions can be controlled by the extent of complementarity to the target and the conditions of incubation.

D. Cleavage of RNA

An RNA version of the sequence used in the transcleavage experiments discussed above was tested for its ability to serve as a substrate in the reaction. The RNA is cleaved at the expected place, in a reaction that is dependent upon the presence of the pilot oligonucleotide. Strikingly, in the case of RNA cleavage, a 3' arm is not required for the pilot oligonucleotide. It is very unlikely that this cleavage is due to previously described RNaseH, which would be expected to cut the RNA in several places along the 30 base-pair long RNA-DNA duplex. The 5' nuclease of DNAPTaq is a structure-specific RNaseH that cleaves the RNA at a single site near the 5' end of the hetero-duplexed region.

Both DNAPTaq and DNAPTth cleave RNA complexed to oligonucleotides in the presence $Mg^{+2}$, but only DNAPTaq degrades the RNA in the presence of $Mm^{+2}$. This difference can help explain why DNAPTth can use RNA as a template in the presence of $Mn^{+2}$. Consequently, use of these enzymes as a reverse transcriptase requires conditions that do not lead to cleavage of the template.

---

We claim:

1. A method of cleaving a target nucleic acid at a specific target site comprising the steps of:
  (a) selecting a target site on a target nucleic acid,
  (b) creating a pilot nucleic acid with a sequence complementary to the sequence of a first region of the target nucleic acid,
  (c) forming a cleavage structure comprising the target nucleic acid and the pilot nucleic acid, wherein the pilot nucleic acid does not contain any region that is not annealed to the target nucleic acid,
    wherein the first region of the target nucleic acid is annealed to the pilot nucleic acid to form a duplex and
    wherein a second region of the target nucleic acid contiguous to the duplex is not annealed to the pilot nucleic acid, forming a junction site between the duplex region and the non-annealed region, and
  (d) exposing the cleavage structure to a cleavage agent which cleaves the cleavage structure at a specific target site within the first region of the target nucleic acid which is annealed to the pilot nucleic acid to form a duplex, within two nucleotides of the junction site, in a manner independent of the sequence of the cleavage structure, wherein the cleavage agent is selected from the group consisting of a 5' nuclease activity of a DNA polymerase and the gene 6 product from bacteriophage T7, and
  (e) incubating the cleavage structure and cleavage agent wherein cleavage occurs.

* * * * *

UNITED STATES PATENT AND TRADEMARK OFFICE
CERTIFICATE OF CORRECTION

| | | |
|---|---|---|
| PATENT NO. | : | 5,422,253 |
| DATED | : | June 6, 1995 |
| INVENTOR(S) | : | James E. Dahlberg, et al. |

It is certified that error appears in the above-identified patent and that said Letters Patent is hereby corrected as shown below:

After the title and before the first line of the specification, please insert:
--This invention was made with United States Government support awarded by the National Institute of Health (NIH), Grant No. R01 GM30220. The United States Government has certain rights in this invention.--

At front page, under OTHER PUBLICATIONS, Lundquist, et al.: "duri" s/b --during--

At column 16, line 53: "Mm$^{+2}$" s/b --Mn$^{+2}$--

Signed and Sealed this

Fifth Day of September, 1995

*Attest:*

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
  ( A ) LENGTH: 91 base pairs
  ( B ) TYPE: nucleic acid
  ( C ) STRANDEDNESS: single
  ( D ) TOPOLOGY: linear ( i i ) MOLECULE TYPE: oligonucleotide ( i i i ) HYPOTHETICAL: YES ( x i ) SEQUENCE DESCRIPTION: SEQ ID NO:1:

TAATACGACT CACTATAGGG AGACCGGAAT TCGAGCTCGC CCGGGCGAGC TCGAATTCCG     60

TGTATTCTAT AGTGTCACCT AAATCGAATT C     91

( 2 ) INFORMATION FOR SEQ ID NO:2:

( i ) SEQUENCE CHARACTERISTICS:
    ( A ) LENGTH: 27 base pairs
    ( B ) TYPE: nucleic acid
    ( C ) STRANDEDNESS: single
    ( D ) TOPOLOGY: linear ( i i ) MOLECULE TYPE: oligonucleotide ( i i i ) HYPOTHETICAL: YES ( x i ) SEQUENCE DESCRIPTION: SEQ ID NO:2:

GAATTCGAT TTAGGTGACAC TATAGAA     27